US00PP36393P2

(12) United States Plant Patent
Donn et al.

(10) Patent No.: US PP36,393 P2
(45) Date of Patent: Jan. 14, 2025

(54) ***DIEFFENBACHIA* PLANT NAMED 'DIEMAWO'**

(50) Latin Name: ***Dieffenbachia* hybrid**
Varietal Denomination: DIEMAWO

(71) Applicants: Michael Donn, Apopka, FL (US); Tyler Donn, Apopka, FL (US)

(72) Inventors: Michael Donn, Apopka, FL (US); Tyler Donn, Apopka, FL (US)

(73) Assignee: AG2 TC, LLC, Apopka, FL (US)

( * ) Notice: Subject to any disclaimer, the term of this patent is extended or adjusted under 35 U.S.C. 154(b) by 0 days.

(21) Appl. No.: 18/586,432

(22) Filed: Feb. 24, 2024

(51) Int. Cl.
*A01H 5/12* (2018.01)
*A01H 6/10* (2018.01)

(52) U.S. Cl.
USPC ..... Plt./378

(58) Field of Classification Search
USPC ..... Plt./378
See application file for complete search history.

*Primary Examiner* — Karen M Redden
*Assistant Examiner* — Zachariah Allan Kay
(74) *Attorney, Agent, or Firm* — James R. Holm; Plant Novelty Rights, LLC

(57) ABSTRACT

A new and distinct *Dieffenbacia* plant named 'DIEMAWO' particularly distinguished by unique leaf variegation pattern having strong brilliant yellow green highlights and deep green spots and a tall, upright, and outwardly arching growth habit.

4 Drawing Sheets

Genus and species: *Dieffenbachia* hybrid.
Variety denomination: 'DIEMAWO'.

BACKGROUND OF THE NEW PLANT

The present invention comprises a new and distinct variety of *Dieffenbachia* plant, botanically known as *Dieffenbachia* sp., and hereinafter referred to by its name 'DIEMAWO'.

The new *Dieffenbachia* cultivar originated as naturally-occurring, whole plant mutation of the commercial *Dieffenbachia* cultivar 'Camouflage' (expired U.S. Plant Pat. No. 12,275). The new *Dieffenbachia* was discovered in April 2021 by the inventor in a commercial greenhouse in Apopka, Florida as a single plant within a large population of plants of the cultivar 'Camouflage', which itself was derived from meristem tissue culture.

The new cultivar was selected based on its unique and distinctive variegated foliage. Plants of the new *Dieffenbachia* and plants of the parent cultivar 'Camouflage' differ in leaf variegation pattern and leaf colors. Asexual reproduction of 'DIEMAWO' by meristem tissue culture was first performed in December 2021 in Apopka, Florida. Asexual reproduction of the new *Dieffenbachia* has shown that the unique features are stable and reproduced true-to-type through 15 successive generations.

Plant Breeder's Rights for this variety have not been applied for. 'DIEMAWO' has not been made publicly available or sold anywhere in the world more than one year prior to the effective filing date of this application.

SUMMARY OF THE INVENTION

The new *Dieffenbachia* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Dieffenbachia* cultivar. The combination of these characteristics distinguishes 'DIEMAWO' as a new and distinct variety of *Dieffenbachia:*

1. Unique leaf variegation pattern having strong brilliant yellow green highlights and deep green spots; and
2. Tall, upright and outwardly arching growth habit.

DESCRIPTION OF THE PHOTOGRAPHS

This new *Dieffenbachia* cultivar is illustrated by the accompanying-colored photographs which show the overall appearance and distinct characteristics of the plant. The colors shown are as true as can be reasonably obtained by conventional photographic procedures. The photographs are of a 1-year-old plant grown in a 3-gallon container in a climate-controlled greenhouse in Apopka, Florida with an average daily temperature of 83 to 85 degrees Fahrenheit. Colors in the photographs may differ slightly from the color values cited in the botanical description which accurately describes the colors of the new variety.

Figure 1:
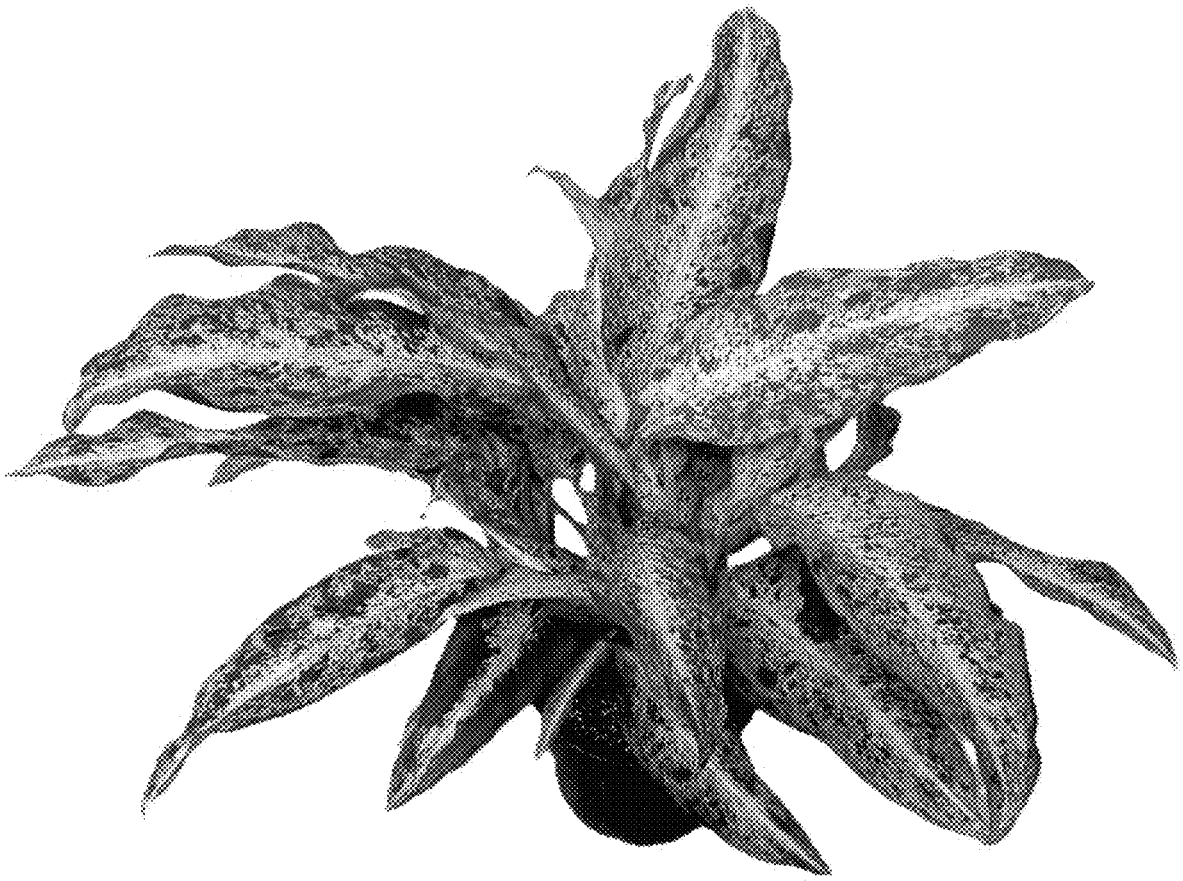

FIG. 1. shows the overall plant form and foliage of 'DIEMAWO'.

Figure 2:
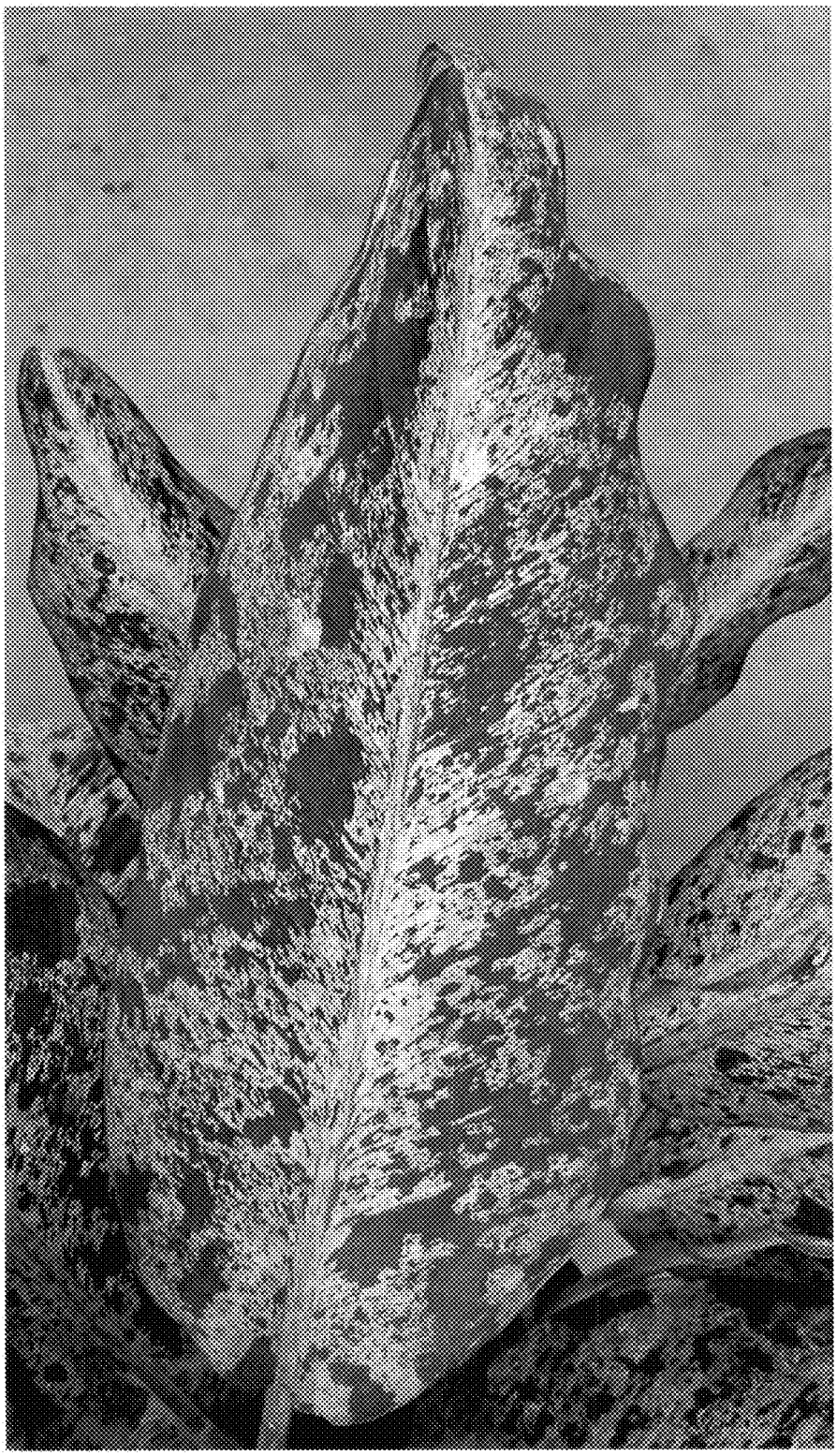

FIG. 2. shows a closeup view of the adaxial surface of a typical juvenile leaf of 'DIEMAWO'.

Figure 3:
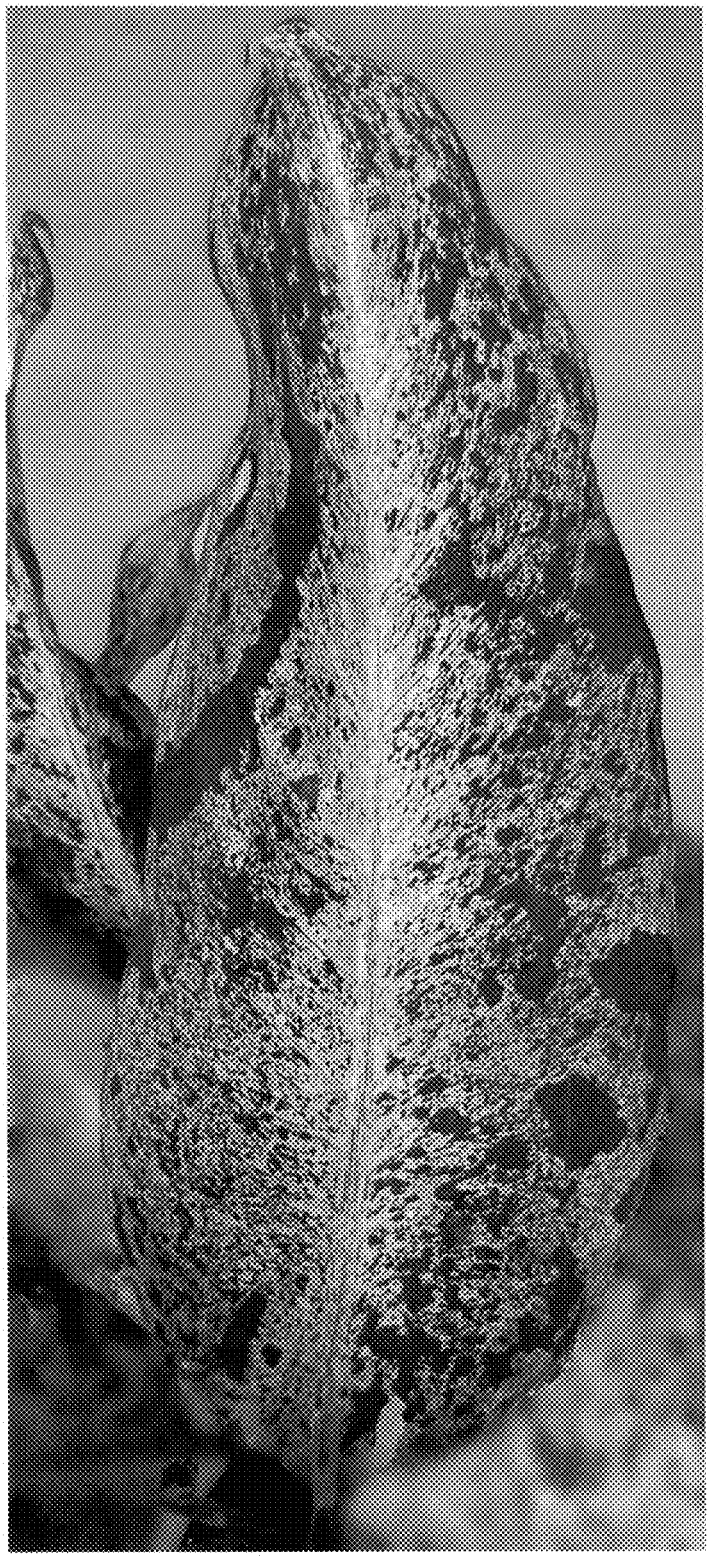

FIG. 3. shows a closeup view of the adaxial surface of a typical mature leaf of 'DIEMAWO'.

Figure 4:
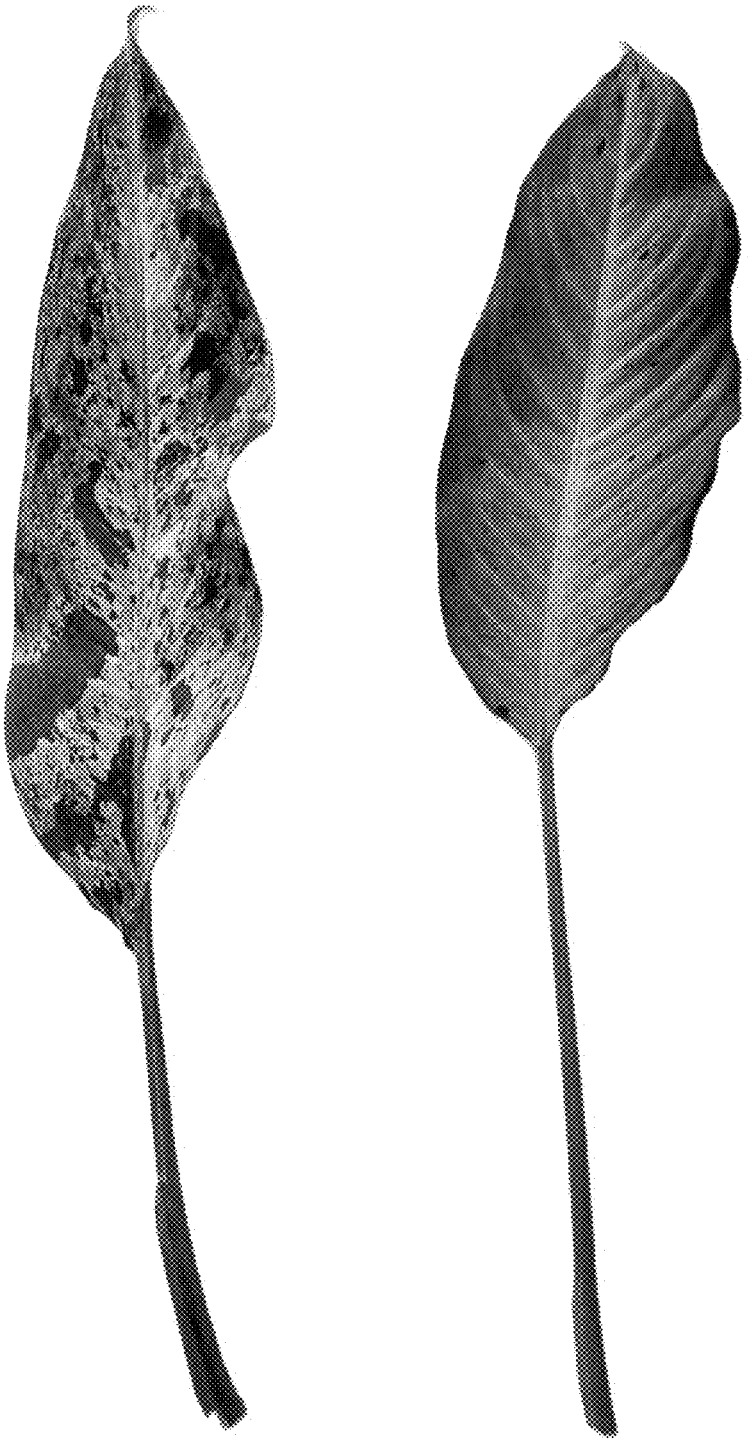

FIG. 4. shows a typical mature leaf of 'DIEMAWO' (left) compared to its parent *Dieffenbachia* plant 'Camouflage' (right).

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a climate-controlled greenhouse in Apopka, Florida with an average daily temperature of 83 to 85 degrees Fahrenheit. Detailed descriptions were taken in December 2023 from 1-year-old plants grown in 3-gallon containers. Measurements and numerical values represent averages of typical plant types.

DETAILED BOTANICAL DESCRIPTION

Classification:

*Family*.—Araceae.

*Botanical*.—*Dieffenbachia* hybrid.

*Common*.—*Dieffenbachia* or Dumb Cane.

*Denomination*.—'DIEMAWO'.

General description:

*Plant type*.—Tropical perennial.

*Growth habit*.—Upright and outwardly arching.

*Height from soil level to top of foliar plane*.—Approximately 50.0 cm.

*Plant spread*.—Approximately 80.0 to 90.0 cm.

*Primary stem*.—Rhizomatous, approximately 25.0 cm in length and 1.3 cm in diameter at the base.

*Number of young axillary stems per primary stem*.—4 to 5.

*Primary and young axillary stem color*.—146A (moderate olive green). Stems are generally not visible as the petiole wings clasp the stem.

*Growth rate*.—Moderate.

*Propagation type*.—Meristem tissue culture.

*Time to initiate roots*.—2 weeks.

*Time to produce a rooted cutting*.—7 to 8 weeks in a 72-cell liner tray.

*Roots*.—Thick, white fleshy roots with fine lateral roots.

Foliage description:

*Quantity of leaves per stem*.—Primary stems: 2 to 3. Young axillary stems: 2 to 3.

*Arrangement*.—Alternate.

*Attachment*.—Petiolate.

*Lamina*.—Shape: Lanceolate. Length: Approximately 40.0 cm to 45.0 cm. Width: Approximately 15.0 cm at the widest point above the base of the lamina. Orientation: Initially held vertically and becoming horizontal when mature. Aspect: The width of the leaf tissue on either side of the midrib is unequal resulting in a slight curving of the leaf blade towards the narrower side. Apex: Acuminate and folding downwards in a hook formation. Base: Slightly to moderately cordate and sometimes truncate. Margins: Entire, slightly undulating. Texture and luster, adaxial surface: Moderately rugose, shiny and becoming more matt on mature leaves. Texture and luster, abaxial surface: Glabrous and glossy. Midrib: Recessed on the upper surface and protruding on the lower surface. Venation pattern: Pinnate, approximately 50 primary veins with numerous secondary veins. Veins are recessed on the upper surface and protruding on the lower surface. Color: Juvenile foliage, adaxial surface: Large and irregular size patches of 143B (strong yellow green) mottled with N189A (dark greyish green); a background coloration of 157B (pale yellow green) and 157D (greenish white) along the midrib and extending out about halfway on both sides of the midrib; and strong highlights of 154B (brilliant yellow green) mixed with N189A (dark greyish green) mostly in proximity of the leaf margin. Juvenile foliage, abaxial surface: Large and irregular sized patches of 138A (moderate yellowish green); a background coloration of 198D (yellowish grey) with smaller streaks and spots of 157C (pale yellow green); and a midrib coloration of 138D (light yellow green). Mature foliage, adaxial surface: Large and irregular sized patches and streaks of N189A (dark greyish green); a background coloration 198D (yellowish grey), primary concentrated within and along both sides of the midrib; and strong highlights of 154B (brilliant yellow green) mixed with spots of N189A (dark greyish green) in random positions across the adaxial surface. Mature foliage, abaxial surface: Large and irregular sized patches and streaks of NN137B (greyish olive green); a background coloration of 198C (yellowish grey); few highlights 154B (brilliant yellow green); and a midrib coloration of 138D (light yellow green) with streaks of 193A (pale yellow green).

*Petioles*.—Strength: Flexible. Aspect: Initially upright and straight and becoming more arching with development. Length (including wing): Approximately 15.0 cm to 17.0 cm. Width (at the base of the lamina): Approximately 1.0 cm. Texture and luster: Glabrous and matt. Color (including outer surface of the wing): Close to 193D (pale yellow green) with streaks of 138B (moderate yellow green). Wing length: Approximately 7.0 cm to 10.0 cm. Wing width: Approximately 1.0 cm to 1.5 cm at the base. Wing color (inner surface): 145C to 145D (light yellow green).

Inflorescence: None observed to date.

Cold tolerance: Not cold tolerant.

Disease and pest tolerance: None observed to date.

Drought tolerance: None observed to date.

COMPARISON WITH PARENT VARIETY

'DIEMAWO' differs from the parent *Dieffenbachia* plant 'Camouflage' in that 'DIEMAWO' has leaves that are more narrowly lanceolate than leaves of 'Camouflage', which are more broadly lanceolate. Additionally, leaves of 'DIEMAWO' have more numerous and much larger patches and streaks of dark greyish green, whereas the patches and streaks of dark greyish green are less numerous and much smaller on leaves of Camouflage.

COMPARISON WITH COMMERCIAL VARIETY

'DIEMAWO' differs from the commercial *Dieffenbachia* plant named 'Tropic Marianne' (expired U.S. Plant Pat. No. 08,832) in that leaves of 'DIEMAWO' have large and irregular sized patches of grey and yellow-green colorations on the adaxial surface, whereas leaves of 'Tropic Marianne' have a broad, solid creamy off-white center coloration on the adaxial surface. Leaves of 'DIEMAWO' are narrow lanceolate, whereas leaves of 'Tropic Marianne' are broad ovate. Finally, the internode lengths of 'DIEMAWO' are much longer than the internode lengths of 'Tropic Marianne'. Thus, 'DIEMAWO' will form distinguishable canes, whereas cane formation of 'Tropic Marianne' is much more reduced compared to 'DIEMAWO'.

What is claimed is:

1. A new and distinct variety of *Dieffenbachia* plant named 'DIEMAWO', substantially as illustrated and described herein.

* * * * *